(12) United States Patent
Wang et al.

(10) Patent No.: US 8,809,792 B2
(45) Date of Patent: Aug. 19, 2014

(54) FIELD-OF-VIEW-DEPENDENT COINCIDENCE WINDOW FOR POSITRON EMISSION TOMOGRAPHY

(71) Applicants: Wenli Wang, Briarcliff Manor, NY (US); Daniel Gagnon, Twinsburg, OH (US); Xiaofeng Niu, Mundelein, IL (US)

(72) Inventors: Wenli Wang, Briarcliff Manor, NY (US); Daniel Gagnon, Twinsburg, OH (US); Xiaofeng Niu, Mundelein, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 137 days.

(21) Appl. No.: 13/630,787

(22) Filed: Sep. 28, 2012

(65) Prior Publication Data

US 2014/0095106 A1    Apr. 3, 2014

(51) Int. Cl.
| | |
|---|---|
| *G06F 19/00* | (2011.01) |
| *G01T 1/164* | (2006.01) |
| *G01T 1/29* | (2006.01) |
| *A61B 6/03* | (2006.01) |
| *G06T 11/00* | (2006.01) |

(52) U.S. Cl.
CPC ............... *G01T 1/2985* (2013.01); *A61B 6/03* (2013.01); *G06T 11/005* (2013.01)
USPC .................... 250/363.03; 250/252.1; 702/157

(58) Field of Classification Search
CPC ........ G01T 1/2985; A61B 6/03; G06T 11/005
USPC ........................... 250/363.03, 252.1; 702/157
See application file for complete search history.

(56) References Cited

U.S. PATENT DOCUMENTS

| | | | |
|---|---|---|---|
| 2007/0106154 A1* | 5/2007 | Conti ........................... 600/436 |
| 2008/0130838 A1* | 6/2008 | Muehllehner et al. ........ 378/207 |
| 2011/0220802 A1* | 9/2011 | Frisch et al. ............. 250/363.03 |
| 2012/0181435 A1* | 7/2012 | Dioszegi et al. ............. 250/362 |
| 2013/0020489 A1 | 1/2013 | Yoshida et al. |

FOREIGN PATENT DOCUMENTS

| | | | |
|---|---|---|---|
| JP | 2011172728 A | * | 9/2011 |
| JP | 2012-103179 A | | 5/2012 |
| JP | 2012-145419 A | | 8/2012 |
| WO | WO 2011/125181 A1 | | 10/2011 |

OTHER PUBLICATIONS

International Search Report issued Nov. 5, 2013 in PCT/JP2013/076161 with English translation of categories of cited documents.

* cited by examiner

*Primary Examiner* — David Porta
*Assistant Examiner* — Abra Fein
(74) *Attorney, Agent, or Firm* — Oblon, Spivak, McClelland, Maier & Neustadt, L.L.P.

(57) ABSTRACT

A method and apparatus for determining a coincidence window for imaging a region of interest of an object using a Positron Emission Tomography (PET) scanner. The method includes determining a diameter of a transverse field of view (FOV) for imaging the region of interest of the object; and calculating the coincidence window based on the determined diameter, a ring diameter of the PET scanner, an axial length of the PET scanner, and a time-of-flight resolution of the PET scanner.

13 Claims, 4 Drawing Sheets

3D view     Transverse view     Sagittal view

FIELD-OF-VIEW-DEPENDENT COINCIDENCE WINDOW FOR POSITRON EMISSION TOMOGRAPHY

FIELD

Embodiments described herein relate generally to methods of imaging an object using radiation detectors, such as for gamma cameras and positron emission tomography (PET) scanners.

BACKGROUND

The use of gamma ray detectors in general, and positron emission tomography or PET detectors in particular, is growing in the field of medical imaging. In PET imaging, a radiopharmaceutical agent is introduced into an object to be imaged via injection, inhalation, or ingestion. After administration of the radiopharmaceutical, the physical and bio-molecular properties of the agent will cause it to concentrate at specific locations in the human body. The actual spatial distribution of the agent, the intensity of the region of accumulation of the agent, and the kinetics of the process from administration to its eventual elimination are all factors that may have clinical significance. During this process, a positron emitter attached to the radiopharmaceutical agent will emit positrons according to the physical properties of the isotope, such as half-life, branching ratio, etc.

The radionuclide emits positrons, and when an emitted positron collides with an electron, an annihilation event occurs, wherein the positron and electron are destroyed. Most of the time, an annihilation event produces two gamma rays (at 511 keV) traveling at substantially 180 degrees apart.

By detecting the two gamma rays, and drawing a line between their locations, i.e., the line-of-response (LOR), one can retrieve the likely location of the original disintegration. While this process will only identify a line of possible interaction, by accumulating a large number of those lines, and through a tomographic reconstruction process, the original distribution can be estimated. In addition to the location of the two scintillation events, if accurate timing (within few hundred picoseconds) is available, a time-of-flight (TOF) calculation can add more information regarding the likely position of the event along the line. Limitations in the timing resolution of the scanner will determine the accuracy of the positioning along this line.

For a clinical, whole-body PET scanner, the imaging field-of-view (FOV) is a cylindrical volume, with a centered circular region in the transverse plane whose diameter is less than the bore size of the scanner, and the same axial length as the PET scanner. For conventional PET scanners, the traverse FOV, which is the diameter of the circular region in the transverse plane, is typically one of two possible values, e.g., 256 mm for a brain scan, and approximately 576-700 mm for a whole-body scan. Moreover, for each of these two possible PET FOVs, the same fixed coincidence window (in the range of 4-6 ns) is used.

In contrast, as shown in Table 1, conventional CT systems support multiple FOVs.

TABLE 1

| | CT FOV | | | | | |
|---|---|---|---|---|---|---|
| | S | M | L | LL | XL | XXL |
| Diameter (mm) | 240 | 320 | 400 | 550 | 700 | 850 |

A problem with conventional PET scanners is that the predetermined whole-body FOV is inadequate for the entire range of patients having different sex, age, body type, and size. Moreover, since an associated CT scan is typically used to obtain the anatomical information of a patient, the different FOV settings used for CT should be adopted for PET. However, using the same fixed coincidence window for different FOVs in PET is inadequate since a large coincidence window for a small FOV increases random coincidences in the prompt data, which degrades the image quality and quantification.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
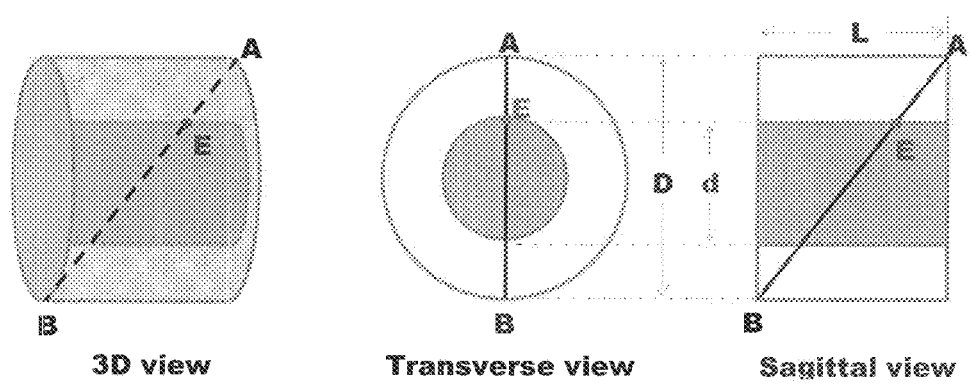
FIG. 1 illustrates various views of a PET field of view.

Embodiments described herein relate to a new method of determining a coincidence window based on the set FOV for a PET scanner.

In particular, the same FOV settings that are supported in an associated CT scanner are also supported by the corresponding PET scanner in a PET/CT system. Moreover, each PET FOV has a corresponding optimal coincidence window size. The coincidence window is determined by the largest time-of-flight difference for the longest oblique line-of-response (LOR) with an emission point located at an edge of the FOV, taking into account the measurement uncertainty in the time-of-flight difference. Thus, the optimal coincidence window size depends on the PET scanner's transverse FOV, axial length, and also on the PET scanner's time-of-flight resolution.

In particular, in one embodiment, there is provided a method of determining a coincidence window for imaging a region of interest of an object using a Positron Emission Tomography (PET) scanner, the method comprising: (1) determining a diameter of a transverse field of view (FOV) for imaging the region of interest of the object; and (2) calculating the coincidence window based on the determined diameter, a ring diameter of the PET scanner, an axial length of the PET scanner, and a time-of-flight resolution of the PET scanner.

In one embodiment, the determining step includes determining the diameter of the transverse FOV from a computed tomography (CT) scanogram of the region of interest of the object.

In one embodiment, the calculating step includes calculating the coincidence window ($\tau$) using the following equation:

$$\tau = \frac{d(\text{mm})}{300(\text{mm/ns})} \sqrt{1 + \left(\frac{L}{D}\right)^2} + \frac{n \cdot FWHM_{\Delta TOF}}{2.355}$$

wherein D is the ring diameter of the PET scanner, L is the axial length of the PET scanner, d is the diameter of the transverse FOV, $FWHM_{\Delta TOF}$ is the time-of-flight resolution of the PET scanner, and n is a predetermined number ($2 \leq n \leq 3$).

In one embodiment, the method further includes performing, using the PET scanner, a PET scan of the region of interest of the object using the calculated coincidence window.

According to another embodiment, there is provided a method of determining a PET coincidence window for imaging a region of interest of an object using a combined Positron Emission Tomography (PET)-Computed Tomography (CT) scanner, the method comprising: (1) setting a CT field of view (FOV) based on a size of the region of interest of the object; (2) setting a diameter of a transverse FOV for PET imaging to be equal to the set CT field of view; and (3) calculating the PET coincidence window based on the determined diameter, a ring diameter of the PET scanner, an axial length of the PET scanner, and a time-of-flight resolution of the PET scanner.

According to another embodiment, there is provided a combined Positron Emission Tomography (PET)-Computed Tomography (CT) scanning apparatus, the apparatus comprising: (1) a CT scanner configured to perform a CT scan of a region of interest of an object using a CT field of view (FOV), which is set based on a size of the region of interest of the object; (2) a PET scanner configured to perform a PET scan of the region of interest of the object using a PET FOV having a diameter in a transverse plane, wherein the diameter is determined from the CT scan of the region of interest; and the PET scanner includes a controller configured to calculate a coincidence window based on the determined diameter, a ring diameter of the PET scanner, an axial length of the PET scanner, and a time-of-flight resolution of the PET scanner.

According to another embodiment, there is provided a combined Positron Emission Tomography (PET)-Computed Tomography (CT) scanning apparatus, the apparatus comprising: (1) a CT scanner configured to perform a CT scan of a region of interest of an object using a CT field of view (FOV), which is set based on a size of the region of interest of the object; (2) a PET scanner configured to perform a PET scan of the region of interest of the object using a PET FOV having a diameter in a transverse plane, wherein the PET scanner includes a controller configured to set the diameter of the PET FOV in the transverse plane to be equal to the set CT FOV, and to calculate a coincidence window based on the set diameter, a ring diameter of the PET scanner, an axial length of the PET scanner, and a time-of-flight resolution of the PET scanner.

Turning now to the figures, FIG. 1 illustrates the imaging FOV for a clinical, whole-body PET scanner. For a cylindrical volume FOV having diameter d within a ring scanner of diameter D and axial length L, the largest time-of-flight difference ($\Delta TOF$) is determined by the longest oblique LOR AB with emission location E at an edge of the FOV, i.e.:

$$|\Delta TOF|_{max} = \frac{|BE - AE|}{c} = \frac{d}{c}\sqrt{1 + \left(\frac{L}{D}\right)^2}$$

where c is speed of light (300 mm/ns).

The coincidence timing window $\tau$, i.e., the threshold to filter coincidence events by two detected photon's arrival timing difference, must consider both the maximum TOF difference and the timing uncertainty. Under the assumption that the time-of-flight difference $\Delta TOF$ is Gaussian distributed, with a standard deviation $\sigma \Delta TOF$ equal to $$\sigma_{\Delta TOF} = FWHM_{\Delta TOF}/2.355$$

then the coincidence window for a cylindrical FOV is computed by:

$$\tau = |\Delta TOF|_{max} + n\sigma_{\Delta TOF}$$

where n=2~3 indicates the confidence interval that all true LORs within the cylindrical FOV are detected by the coincidence window. When n=3, 99.7% of the true LORs within the cylinder are detected by the computed coincidence window. When n=2, the confidence interval is 95%. A value of n between 2 and 3 is recommended.

Based on the above equations, we have:

$$\tau(\text{ns}) = \frac{d(\text{mm})}{300(\text{mm/ns})}\sqrt{1 + \left(\frac{L}{D}\right)^2} + \frac{n \cdot FWHM_{\Delta TOF}(\text{ns})}{2.355}$$

Thus, the coincidence window is a function of the FOV and is computed explicitly using the PET detector's diameter, length, and timing resolution.

The embodiments in which the coincidence window is calculated based on the FOV and the PET detector's properties has advantages over conventional scanners. For example, the amount of random coincidence is reduced for each FOV with the above-calculated "optimal" coincidence window instead of a fixed one, while true coincidences are not affected.

For example, Table 2 lists the computed coincidence window (using D=909 mm, L=196 mm, FWHM $\Delta TOF$=450 ps, and n=2.7), and the amount of random reduction for different size FOVs using a NEMA-NU2 count-rate phantom, compared with a fixed 3.0 ns coincidence window.

TABLE 2

| PET FOV | S(240) | M(320) | L(400) | LL(550) | XL(700) |
|---|---|---|---|---|---|
| coinWin (ns) | 1.4 | 1.7 | 2.0 | 2.5 | 3.0 |
| Random reduction | 53% | 43% | 33% | 17% | 0% |

Figure 2:
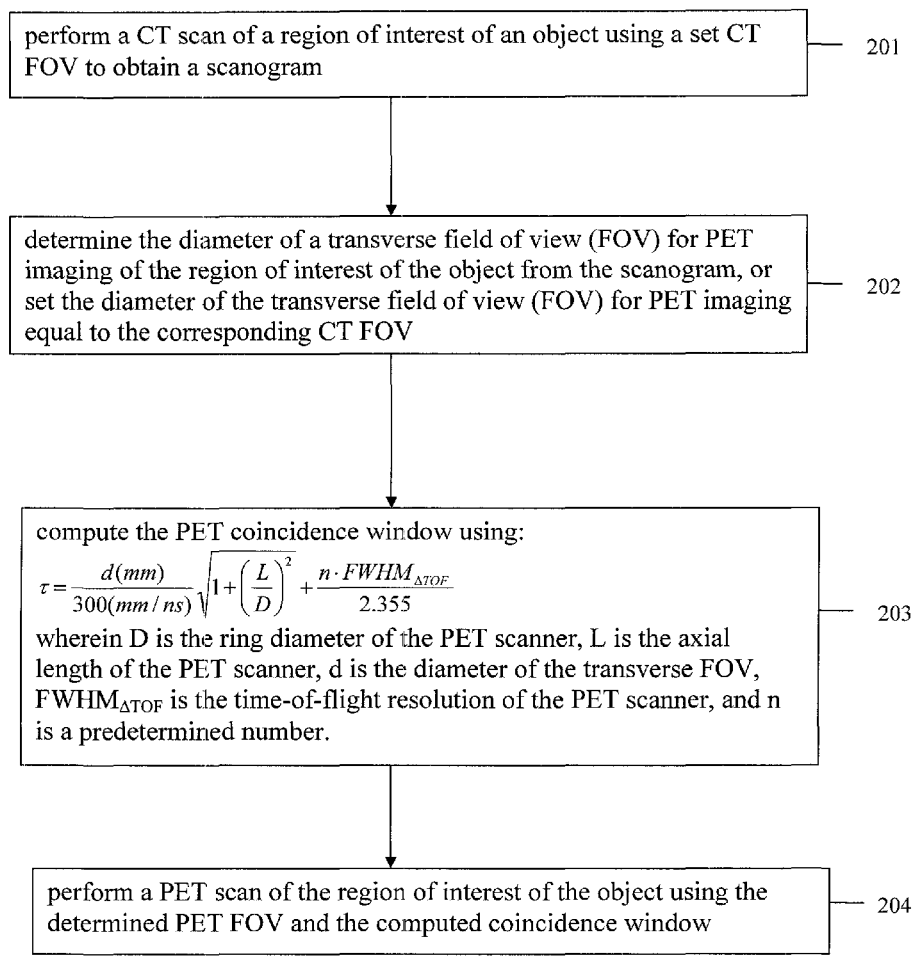
FIG. 2 illustrates a method of computing a PET coincidence window according to one embodiment.

FIG. 2 illustrates a method of performing a PET scan with a PET scanner of a PET-CT scanner according to one embodiment.

In step 201, a CT scan of a region of interest of an object is performed using a set CT FOV to obtain a CT scanogram. As shown in Table 1, any of a number of CT FOVs can be used depending on the region of interest and the object being imaged.

In step 202, the diameter d of the transverse FOV for PET imaging is determined. The diameter can be determined from the CT scanogram obtained in step 201. Alternatively, the diameter can be set to be the same as the CT FOV value used in step 201.

In step 203, the PET coincidence window is determined using the formula:

$$\tau = \frac{d(\text{mm})}{300(\text{mm/ns})}\sqrt{1 + \left(\frac{L}{D}\right)^2} + \frac{n \cdot FWHM_{\Delta TOF}}{2.355}$$

wherein D is the ring diameter of the PET scanner, L is the axial length of the PET scanner, d is the diameter of the transverse FOV, $FWHM_{\Delta TOF}$ is the time-of-flight resolution of the PET scanner, and n is a predetermined number.

In step 204, a PET scan of the region of interest of the object is performed using the PET FOV determined in step 202 and the coincidence window computed in step 203.

Figure 3:
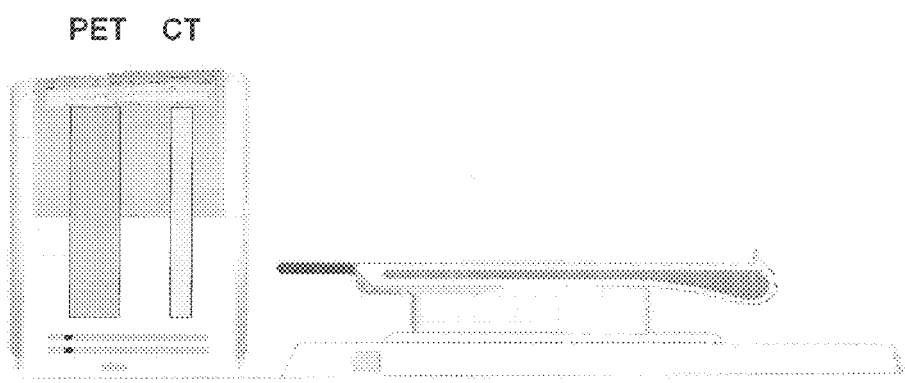
FIG. 3 illustrates a PET-CT scanner system according to one embodiment.
Figure 4:
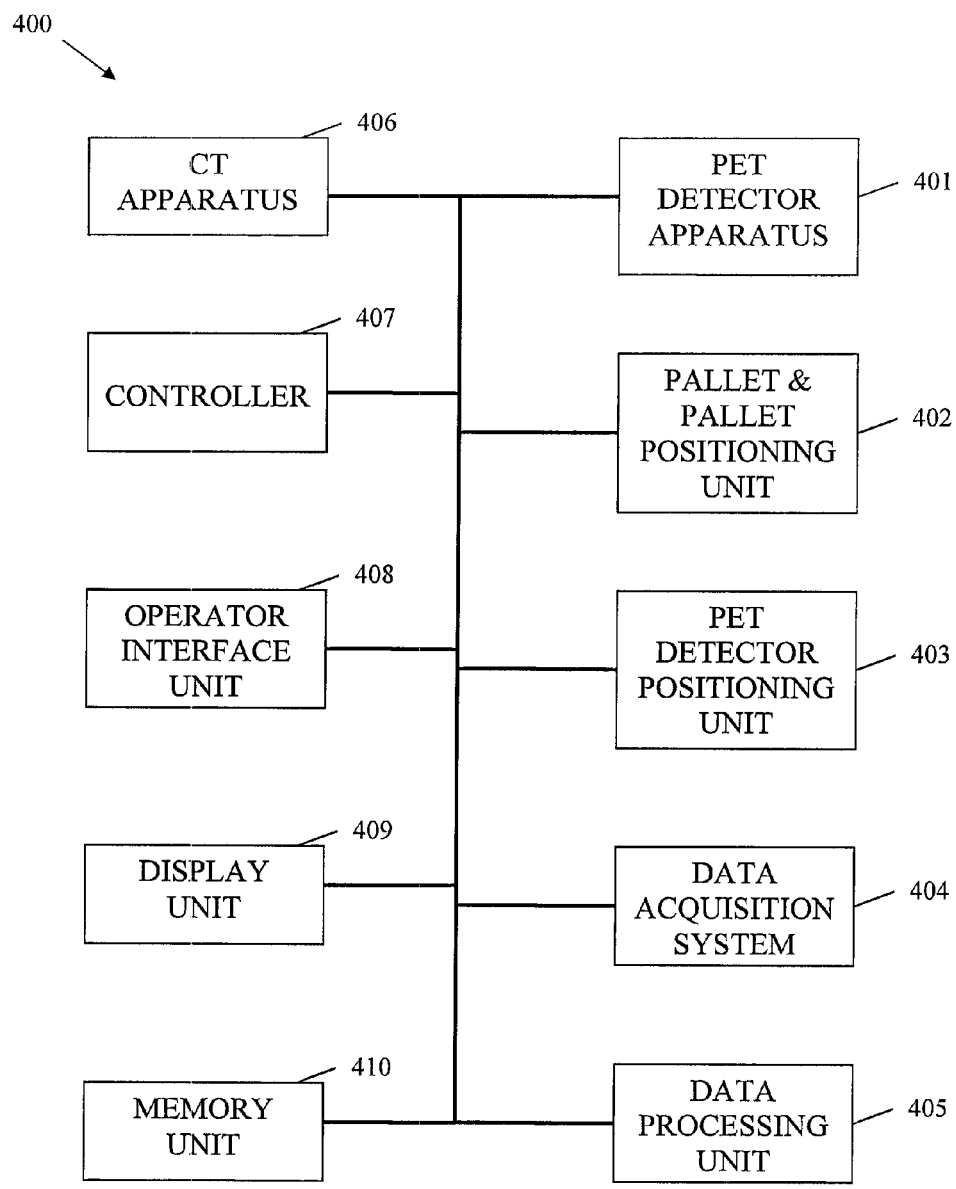
FIG. 4 illustrates components of the PET-CT scanner system of FIG. 3.

FIGS. 3 and 4 illustrate a PET/CT system 400 according to one embodiment, the system including a CT apparatus 406 configured to perform a CT scan and a PET detector apparatus 401 configured to perform a PET scan.

The PET/CT system 400 includes a movable patient pallet 402 that includes a pallet positioning unit configured to position the patient pallet within the PET detector apparatus 401 and the CT apparatus 406, based on, for example, commands received from the controller 407.

The controller 407 controls the overall functioning of the PET/CT system 406, including controlling the position of the patient pallet via the pallet positioning unit. The pallet positioning unit includes mechanisms configured to move the patient pallet at least in a longitudinal direction. The controller 407 also controls the PET detector positioning unit 403, which positions one or more PET detector portions around a patient on the pallet.

The controller 407 is also configured to calculate a coincidence window based on the determined diameter, a ring diameter of the PET scanner, an axial length of the PET scanner, and a time-of-flight resolution of the PET scanner, as discussed above.

The data acquisition system 404 obtains PET event data from the PET detector apparatus 401 during a PET scan and sends the event data to the data processing unit for reconstruction of a PET image. The PET event data can also be stored in the memory unit 410 prior to processing by the data processing unit 405.

The operator interface unit 408 is configured to receive operator commands, for example, initiating a CT scan or a PET scan or setting a region of interest on a CT image, and/or to receive parameters associated with the scans. PET and CT images of the patient, as well as operational parameters associated with the scans are displayed on the display unit 409.

As one of ordinary skill in the art would recognize, the controller 407 and the data processing unit 405 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the memory unit 410 may be non-volatile, such as ROM, EPROM, EEPROM or FLASH memory. The memory unit 410 can also be volatile, such as static or dynamic RAM, and a processor, such as a microcontroller or microprocessor, may be provided to manage the electronic memory as well as the interaction between the FPGA or CPLD and the memory unit.

Alternatively, the CPU in the controller 407 or the data processing unit 405 may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the data processing unit 405, the processed signals are stored in memory unit 410, and/or displayed on display unit 409. As one of ordinary skill in the art would recognize, memory unit 410 can be a hard disk drive, CD-ROM drive, DVD drive, FLASH drive, RAM, ROM or any other electronic storage known in the art. Display unit 409 can be implemented as an LCD display, CRT display, plasma display, OLED, LED or any other display known in the art. As such, the descriptions of the memory unit 410 and the display unit 409 provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of determining a coincidence window for imaging a region of interest of an object using a Positron Emission Tomography (PET) scanner, the method comprising:
   determining a diameter of a transverse field of view (FOV) for imaging the region of interest of the object; and
   calculating the coincidence window based on the determined diameter, a ring diameter of the PET scanner, an axial length of the PET scanner, and a time-of-flight resolution of the PET scanner.

2. The method of claim 1, wherein the determining step comprises;
   determining the diameter of the transverse FOV from a computed tomography (CT) scanogram of the region of interest of the object.

3. The method of claim 1, wherein the calculating step comprises:
   calculating the coincidence window ($\tau$) using the following equation:

$$\tau = \frac{d(\text{mm})}{300(\text{mm/ns})}\sqrt{1+\left(\frac{L}{D}\right)^2} + \frac{n \cdot FWHM_{\Delta TOF}}{2.355}$$

wherein D is the ring diameter of the PET scanner, L is the axial length of the PET scanner, d is the diameter of the transverse FOV, $FWHM_{\Delta TOF}$ is the time-of-flight resolution of the PET scanner, and n is a predetermined number.

4. The method of claim 3, wherein $2 \leq n \leq 3$.

5. The method of claim 1, further comprising:
   performing, using the PET scanner, a PET scan of the region of interest of the object using the calculated coincidence window.

6. A method of determining a PET coincidence window for imaging a region of interest of an object using a combined Positron Emission Tomography (PET)-Computed Tomography (CT) scanner, the method comprising:

setting a CT field of view (FOV) based on a size of the region of interest of the object;
setting a diameter of a transverse FOV for PET imaging to be equal to the set CT field of view; and
calculating the PET coincidence window based on the determined diameter, a ring diameter of the PET scanner, an axial length of the PET scanner, and a time-of-flight resolution of the PET scanner.

7. The method of claim 6, wherein the calculating step comprises:
calculating the coincidence window ($\tau$) using the following equation:

$$\tau = \frac{d(\text{mm})}{300(\text{mm/ns})}\sqrt{1+\left(\frac{L}{D}\right)^2} + \frac{n \cdot FWHM_{\Delta TOF}}{2.355}$$

wherein D is the ring diameter of the PET scanner, L is the axial length of the PET scanner, d is the diameter of the transverse FOV, $FWHM_{\Delta TOF}$ is the time-of-flight resolution of the PET scanner, and n is a predetermined number.

8. The method of claim 7, wherein $2 \leq n \leq 3$.

9. The method of claim 6, further comprising:
performing a PET scan of the region of interest of the object using the calculated coincidence window.

10. A combined Positron Emission Tomography (PET)-Computed Tomography (CT) scanning apparatus, the apparatus comprising:
a CT scanner configured to perform a CT scan of a region of interest of an object using a CT field of view (FOV), which is set based on a size of the region of interest of the object;
a PET scanner configured to perform a PET scan of the region of interest of the object using a PET FOV having a diameter in a transverse plane,
wherein the diameter is determined from the CT scan of the region of interest; and
the PET scanner includes a controller configured to calculate a coincidence window based on the determined diameter, a ring diameter of the PET scanner, an axial length of the PET scanner, and a time-of-flight resolution of the PET scanner.

11. The method of claim 10, wherein the controller is configured to calculate the coincidence window ($\tau$) using the following equation:

$$\tau = \frac{d(\text{mm})}{300(\text{mm/ns})}\sqrt{1+\left(\frac{L}{D}\right)^2} + \frac{n \cdot FWHM_{\Delta TOF}}{2.355}$$

wherein D is the ring diameter of the PET scanner, L is the axial length of the PET scanner, d is the diameter of the transverse FOV, $FWHM_{\Delta TOF}$ is the time-of-flight resolution of the PET scanner, and n is a predetermined number.

12. A combined Positron Emission Tomography (PET)-Computed Tomography (CT) scanning apparatus, the apparatus comprising:
a CT scanner configured to perform a CT scan of a region of interest of an object using a CT field of view (FOV), which is set based on a size of the region of interest of the object;
a PET scanner configured to perform a PET scan of the region of interest of the object using a PET FOV having a diameter in a transverse plane,
wherein the PET scanner includes a controller configured to set the diameter of the PET FOV in the transverse plane to be equal to the set CT FOV, and to calculate a coincidence window based on the set diameter, a ring diameter of the PET scanner, an axial length of the PET scanner, and a time-of-flight resolution of the PET scanner.

13. The apparatus of claim 12, wherein the controller is configured to calculate the coincidence window ($\tau$) using the following equation:

$$\tau = \frac{d(\text{mm})}{300(\text{mm/ns})}\sqrt{1+\left(\frac{L}{D}\right)^2} + \frac{n \cdot FWHM_{\Delta TOF}}{2.355}$$

wherein D is the ring diameter of the PET scanner, L is the axial length of the PET scanner, d is the diameter of the transverse FOV, $FWHM_{\Delta TOF}$ is the time-of-flight resolution of the PET scanner, and n is a predetermined number.

* * * * *